(12) United States Patent
Chung et al.

(10) Patent No.: US 8,338,667 B2
(45) Date of Patent: Dec. 25, 2012

(54) ENVIRONMENTAL STRESS-INDUCIBLE 972 PROMOTER ISOLATED FROM RICE AND USES THEREOF

(75) Inventors: Hwa Jee Chung, Daejeon (KR); Ju Young Park, Daejeon (KR); Mi Na Kim, Daejeon (KR); Yong Woog Lee, Daejeon (KR)

(73) Assignee: Gendocs, Inc., Daejoen (KR)

( * ) Notice: Subject to any disclaimer, the term of this patent is extended or adjusted under 35 U.S.C. 154(b) by 267 days.

(21) Appl. No.: 12/920,005

(22) PCT Filed: Mar. 31, 2010

(86) PCT No.: PCT/KR2010/001974
§ 371 (c)(1),
(2), (4) Date: Aug. 27, 2010

(87) PCT Pub. No.: WO2010/120054
PCT Pub. Date: Oct. 21, 2010

(65) Prior Publication Data
US 2011/0055967 A1    Mar. 3, 2011

(30) Foreign Application Priority Data
Apr. 16, 2009    (KR) .................. 10-2009-0033017

(51) Int. Cl.
*A01H 5/00*    (2006.01)
*C12N 15/82*    (2006.01)
*C07H 21/04*    (2006.01)
(52) U.S. Cl. ....... 800/298; 800/278; 536/24.1; 536/24.3
(58) Field of Classification Search .................. None
See application file for complete search history.

(56) References Cited

U.S. PATENT DOCUMENTS
4,940,838 A    7/1990    Schilperoort et al.

FOREIGN PATENT DOCUMENTS
| EP | 0 116 718 | 8/1984 |
| EP | 0 120 516 | 10/1984 |
| EP | 0 301 316 | 2/1989 |
| KR | 10-0578461 | 5/2006 |
| KR | 10-0781059 | 11/2007 |

OTHER PUBLICATIONS

Joan T. Odell et al., Nature vol. 313, Feb. 28, 1985, pp. 810-812.
Qiang Liu et al., The Plant Cell, vol. 10, 1391-1406, Aug. 1998.
Sarah Gilmour et al., Plant Physiology, Dec. 2000, vol. 124, pp. 1854-1865.
Mie Kasuga et al., Nature Biotechnology vol. 17, Mar. 1999, pp. 287-291.
Christiane Gatz et al., The Plant Journal (1992) 2(3), 397-404.
Pamela Weinmann et al., The Plant Journal (1994) 5(4), 559-569.
Takashi Aoyama et al., The Plant Journal (1997) 11(3), 605-612.
F. A. Krens et al., Nature vol. 296, Mar. 4, 1982, pp. 72-74.
I. Negruitu et al., Plant Molecular Biology 8: 363-373 (1987).
R. D. Shillito et al., Biotechnology vol. 3, Dec. 1985, pp. 1099-1102.
Anne Crossway et al., Mol Gen Genet (1986) 202: 179-185.
T. M. Klein et al., Nature vol. 327, May 7, 1987, pp. 70-73.

*Primary Examiner* — Elizabeth McElwain
(74) *Attorney, Agent, or Firm* — The PL Law Group, PLLC (57) ABSTRACT

The present invention relates to environmental stress-inducible 972 promoter isolated from rice, a recombinant plant expression vector comprising said promoter, a method of producing a target protein by using said recombinant plant expression vector, a method of producing a transgenic plant using said recombinant plant expression vector, a transgenic plant produced by said method, a method of improving resistance of a plant to environmental stress by using said promoter, and a primer set for amplification of said promoter.

12 Claims, 3 Drawing Sheets

SEQUENCE LISTING

```
<160> NUMBER OF SEQ ID NOS: 5

<210> SEQ ID NO 1
<211> LENGTH: 1859
<212> TYPE: DNA
<213> ORGANISM: Oryza sativa

<400> SEQUENCE: 1
ctgcagcacc tctttacaac tatggccttg tttagttctc caaattttt tcctaaaaac      60 atcacaccga atctttggac agatgcatgg agcattaaat atagataaaa taaaagacta     120
attacacagt tagagggaaa atcgcgaggc gaatcttttg agtctaatta gtccatgatt     180
agctataagt gctacagtaa cctatatatg gtaatgacgg attaattagg cttaataaat     240
tcgtctcgcg gtttccaggt gagttataaa attagttttt tcattcatgt ccgaaaaccc     300
cttccaacat ccggtcaaac atccgatatg acaccaaaaa attttctttt cgcgaactaa     360
acaaggccta tatataatta aatgaattac atatatccat gcaactagca aatttgctat     420
aaaacactta aattttatgt aatttaccat agacatcaca aagatgtgtc atgactaaag     480
aacacctaaa aaactagtaa tgtgctagag gttacttta actgaattgg agagataaat      540
tgtactcact gatatttgat aatggaaatg gtaccacacg tttattgtgg agtacctcac     600
tctattgtca ctttgacttt tccatattca atttttttaaa aagttttaac caaatttata    660 taaaagttg gcaacatata taacacaaaa ttagtttaat taatattaaa tatgttttga     720
taatatattt tattttgtt aaaaacatcg ctatatttat attataaact tgactaaact      780
taaaacaaaa ttaattagaa aaagccaaa atgtcctaaa atatgaaaca tagaaagtac     840 tgctcttcc atccaagaga tagcaacctg agactcgtaa gactagatat tcatattcag     900
tacaagttgc tatacgtgtc cagatttaca agaatagaat atgtgagacc catatatcca    960
```

```
gttctagctg aatgtaggga gtacatccat cccaatataa gtaggagtgc aattttgtat      1020
agatgtgata tatcctataa caatgatatc acatctatac tcccttcatt ctaaaaaaac      1080
aatctattat tggatgagac ttttttctac tacaataaat ctatacacgt agaaaaatat      1140
catcgaatat taggttgcaa tggagggagt tctagtgctt actctctccg tcttaaaata      1200
taaacatttt tagtatagtg ccaagtcaaa cattttttaac tttaattatt aataaaaaaa      1260
ataaaaaaat cgattgatgt tactagattt atcattaaac aaaatattat aatatgtaac      1320 tcttttttatt tagaatatat atagatgtat gtcgaagacc atatcaaagt taaaaataag      1380
tgttctgaga cggaggaata tattgcatat aggacgtcgt acttatcagc aaagaaatga      1440
aatggatgga cggtgatcac gtgttgacca gacctgacac aaactcacat tcattactgt      1500
tacgcgtctc cacgtgcctc ctctccctcc accggacctc atatcatatt tccttccctt      1560
agtcgccatt ttcttcccat atccacgcgc cacgtggact tcctgacgac ggccggcgac      1620
acgtgaaccc agaaccttcc ccaacgatct cattctcttg ctgtcttgcg tgttcatgct      1680
gccccgcggg cgttgagttt cttctctact tcctccgtca ccaacgaccc atgcatatct      1740
atctgatctc cacgacgcgc ctaagcaatc catctccatc tccctatata taatggatcg      1800
aaagctcgac atgcattaca tctatctcaa atcatctctc tgcctcatct caagtcgac       1859
```

```
<210> SEQ ID NO 2
<211> LENGTH: 28
<212> TYPE: DNA
<213> ORGANISM: Artificial Sequence
<220> FEATURE:
<223> OTHER INFORMATION: 972pro5'-PstI primer

<400> SEQUENCE: 2
ctgcagcacc tctttacaac tatggcct                                          28

<210> SEQ ID NO 3
<211> LENGTH: 26
<212> TYPE: DNA
<213> ORGANISM: Artificial Sequence
<220> FEATURE:
<223> OTHER INFORMATION: 972pro3'-SalI primer

<400> SEQUENCE: 3
gtcgacttga gatgaggcag agagat                                            26

<210> SEQ ID NO 4
<211> LENGTH: 20
<212> TYPE: DNA
<213> ORGANISM: Artificial Sequence
<220> FEATURE:
<223> OTHER INFORMATION: 972 GSP-F primer

<400> SEQUENCE: 4
actcctcctc ctgctgccac                                                   20

<210> SEQ ID NO 5
<211> LENGTH: 20
<212> TYPE: DNA
<213> ORGANISM: Artificial Sequence
<220> FEATURE:
<223> OTHER INFORMATION: 972 GSP-R primer

<400> SEQUENCE: 5
gaagcacatg tcgaggaggc                                                   20
```

ENVIRONMENTAL STRESS-INDUCIBLE 972 PROMOTER ISOLATED FROM RICE AND USES THEREOF

CLAIM OF PRIORITY

This application makes reference to, incorporates the same herein, and claims all benefits accruing under 35 U.S.C. §119 from an application earlier filed in the Korean Intellectual Property Office on 16 Apr. 2009 and there duly assigned Serial No. 10-2009-0033017. This application also makes reference to, incorporates the same herein, and claims all benefits accruing under 35 U.S.C. §365(c) of my PCT International application entitled ENVIRONMENTAL STRESS—INDUCIBLE 972 PROMOTER ISOLATED FROM RICE AND USES THEREOF filed on 31 Mar. 2010 and duly assigned Serial No. PCT/KR2010/001974.

BACKGROUND OF THE INVENTION

1. Field of the Invention

The present invention relates to environmental stress-inducible 972 promoter isolated from rice and use thereof. Specifically, the present invention relates to environmental stress-inducible 972 promoter isolated from rice, a recombinant plant expression vector comprising said promoter, a method of producing a target protein by using said recombinant plant expression vector, a method of producing a transgenic plant using said recombinant plant expression vector, a transgenic plant produced by said method, a method of improving resistance of a plant to environmental stress by using said promoter, and a primer set for amplification of said promoter.

2. Description of the Related Art

A promoter is a part of genome which is located upstream of a structural gene and regulates transcription of the structural gene into mRNA. A promoter is activated by binding of various general transcription factors, and it typically comprises a base sequence such as TATA box, CAT box, etc. which regulates gene expression. Since proteins that are required for basic metabolism of a living body need to be maintained at constant concentration, a promoter that is associated with genes of such proteins is constantly activated even by general transcription factors only. On the other hand, for the proteins of which function is not required during normal time but required only under specific circumstances, an inducible promoter which can induce expression of a corresponding structural gene is linked to the corresponding genes. In other words, an inducible promoter is activated by binding of specific transcription factors that are stimulated during a developmental process of an organism or stimulated by environmental factors.

For the development of a transgenic plant based on gene transformation, a promoter which can induce constant and strong expression, for example cauliflower mosaic virus 35S promoter (CaMV35S, Odell et al., Nature 313: 810-812, 1985), is widely used. However, since constant overexpression of a specific gene linked to such promoter can produce an excess amount of proteins that are not necessarily required for metabolism of a normal living body, it often becomes problematic in that a transgenic plant does not properly germinate or only a small-sized plant is produced due to toxic effect generated by the proteins present in an excess amount. As a representative example, it was found that *Arabidopsis thaliana* in which DREB 1A, a gene encoding transcription factors responding to environmental stress, is overexpressed by using CaMV35S promoter has improved resistance to low temperature and drought condition, but also had a dwarfed phenotype with inhibited growth and increased production of proline and water-soluble carbohydrates (Liu et al., Plant Cell 10: 1391-1406, 1998; Gilmour et al., Plant Physiol. 124: 1854-1865, 2000). Occurrence of such problems can be minimized by using an inducible promoter for rd29A, that is a gene relating to environmental stress, instead of CaMV35S promoter (Kasuga et al, Nat. Biotechnol. 17: 287-291, 1999).

Under the circumstances, instead of a promoter which constantly induces gene expression in a plant tissue, an inducible promoter which can induce expression of a target gene at specific time and under specific condition has been actively studied and developed. As a scientific research, an inducible promoter system, which can stimulate biosynthesis of a target protein based on introduction of a promoter isolated from a microorganism or an animal to a plant and use of a chemical substance as an inducing agent, has been widely developed. Until now, as an example of application of an expression inducing system based on use of a chemical substance on a plant, a method in which a steroid such as dexamethasone, antibiotics such as tetracycline, and a chemical substance such as copper ion, IPTG and the like are used as an inducing agent has been known (Gatz et al., Plant J. 2: 397-404, 1992; Weimann et al., Plant J. 5: 559-569, 1994; Aoyama T. and Chua N-H, Plant J. 11: 605-612, 1997). However, such method is problematic in that the chemical substance used as an inducing agent for a system is extremely expensive and such chemicals often have a toxic effect by themselves, so that the method cannot be applied to all plants.

In Korean Patent Registration No. 10-0781059, an inducible promoter that is activated by environmental stress and a method of obtaining a transgenic protein in guard cells by using such promoter are described. In addition, in Korean Patent Registration No. 10-0578461, a stress-inducible promoter that is isolated from rice is disclosed. However, these are all different from the promoter described in the present invention.

The present invention was devised in view of above-described needs. Specifically, after intensive studies to develop a promoter which is induced by environmental stress, particularly by drought stress, inventors of the present invention found that a certain promoter isolated from rice is strongly induced by drought stress, and therefore completed the present invention.

SUMMARY OF THE INVENTION

In order to solve the above problems, the present invention provides environmental stress-inducible 972 promoter isolated from rice.

Further, the present invention provides a recombinant plant expression vector comprising said promoter.

Further, the present invention provides a method of producing a target protein by using said recombinant plant expression vector.

Further, the present invention provides a method of producing a transgenic plant using said recombinant plant expression vector.

Further, the present invention provides a transgenic plant produced by said method.

Further, the present invention provides a method of improving resistance of a plant to environmental stress by using said promoter, Still further, the present invention provides a primer set for amplification of said promoter.

The present invention provides an isolated nucleic acid construct comprising a strong constitutive plant promoter which can bind to a heterologous gene encoding a desired polypeptide in a tissue of a transgenic plant. When used as a construct for a heterologous coding sequence in a chimeric gene, said construct functions as a drought stress inducible-promoter and is useful for obtaining high expression of a desired polypeptide in a leaf tissue of a plant. A vector in which a certain chimeric gene is linked to said construct can be introduced to a plant tissue, and as a result, a plant can be deliberately transformed with such vector and a foreign material can be produced from the resulting transgenic plant.

In addition, it is expected that, by using the promoter that is provided by the present invention and a technology of breeding an environmental stress-resistant transgenic plant using the promoter, improvement of crop yield for the economically important crops can be achieved.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, in which like reference symbols indicate the same or similar components, wherein.

DETAILED DESCRIPTION OF THE INVENTION

Mode for the Invention

In order to achieve the object of the invention described above, the present invention provides environmental stress-inducible 972 promoter isolated from rice, which consists of a nucleotide sequence of SEQ ID NO: 1.

The present invention is related to a specific promoter that is isolated from rice, and more specifically, the promoter consists of a nucleotide sequence of SEQ ID NO: 1. Further, variants of the said promoter sequence are within the scope of the present invention. The variants have a different nucleotide sequence but have similar functional characteristics to those of the nucleotide sequence of SEQ ID NO: 1. Specifically, the promoter of the present invention may comprise a nucleotide sequence with at least 70%, preferably at least 80%, more preferably at least 90%, and most preferably at least 95% homology with the nucleotide sequence of SEQ ID NO: 1.

The "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

With respect to the promoter according to one embodiment of the present invention, the environmental stress can be drought, high temperature, cold temperature, high salt, heavy metals, etc. Preferably, it is drought stress.

In order to achieve another object of the present invention, the present invention provides a recombinant plant expression vector which comprises the promoter according to the present invention. As an example of the recombinant plant expression vector, pHC10:972 promoter vector shown in FIG. 2 of the present invention can be mentioned, but not limited thereto.

The term "recombinant" indicates a cell which replicates a heterogeneous nucleotide or expresses the nucleotide, a peptide, a heterogeneous peptide, or a protein encoded by a heterogeneous nucleotide. Recombinant cell can express a gene or a gene fragment, that are not found in natural state of cell, in a form of a sense or antisense. In addition, a recombinant cell can express a gene that is found in natural state, provided that said gene is modified and re-introduced into the cell by an artificial means.

The term "vector" is used herein to refer DNA fragment (s) and nucleotide molecules that are delivered to a cell. Vector can be used for the replication of DNA and be independently reproduced in a host cell. The terms "delivery system" and "vector" are often interchangeably used. The term "expression vector" means a recombinant DNA molecule comprising a desired coding sequence and other appropriate nucleotide sequences that are essential for the expression of the operatively-linked coding sequence in a specific host organism. Promoter, enhancer, termination codon and polyadenylation signal that can be used for an eukaryotic cell are well known in the pertinent art.

A preferred example of plant expression vector is Ti-plasmid vector which can transfer a part of itself, i.e., so called T-region, to a plant cell when the vector is present in an appropriate host such as *Agrobacterium tumefaciens*. Other types of Ti-plasmid vector (see, EP 0 116 718 B1) are currently used for transferring a hybrid gene to protoplasts that can produce a new plant by appropriately inserting a plant cell or hybrid DNA to a genome of a plant. Especially preferred form of Ti-plasmid vector is a so called binary vector which has been disclosed in EP 0 120 516 B1 and U.S. Pat. No. 4,940,838. Other vector that can be used for introducing the DNA of the present invention to a host plant can be selected from a double-stranded plant virus (e.g., CaMV), a single-stranded plant virus, and a viral vector which can be originated from Gemini virus, etc., for example a non-complete plant viral vector. Use of said vector can be advantageous especially when a plant host cannot be appropriately transformed.

Expression vector would comprise at least one selective marker. Said selective marker is a nucleotide sequence having a property based on that it can be selected by a common chemical method. Every gene which can be used for the differentiation of transformed cells from non-transformed cell can be a selective marker. Example includes, a gene resistant to herbicide such as glyphosate and phosphintricin, and a gene resistant to antibiotics such as kanamycin, G418, bleomycin, hygromycin, and chloramphenicol, but not limited thereto.

For the plant expression vector according to one embodiment of the present invention, any conventional terminator can be used. Example includes, nopaline synthase (NOS), rice α-amylase RAmyl A terminator, phaseoline terminator, and a terminator for optopine gene of *Agrobacterium tumefaciens*, etc., but are not limited thereto. Regarding the necessity of terminator, it is generally known that such region can increase a reliability and an efficiency of transcription in plant cells. Therefore, the use of terminator is highly preferable in view of the contexts of the present invention.

With respect to the recombinant plant expression vector according to one embodiment of the present invention, it can be the one which is constructed by operatively linking a gene encoding a target protein to a downstream region of the promoter of the present invention. In the present specification, the term "operatively-linked" is related to a component of an expression cassette, which functions as a unit for expressing a heterogenous protein. For example, a promoter which is operatively-linked to a heterogeneous DNA encoding a protein stimulates production of functional mRNA which corresponds to the heterogeneous DNA.

The above-described target protein can be any kind of protein, and examples thereof include a protein which is therapeutically useful, i.e., an enzyme, a hormone, an antibody, a cytokine, etc., a protein which can accumulate a great amount of nutritional components useful for health enhancement in an animal including a human, and an enzyme which can degrade cellulose, etc., but not limited thereto. Specific examples of a target protein include interleukin, interferon, platelet-derived growth factor, hemoglobin, elastin, collagen, insulin, fibroblast growth factor, human growth factor, human serum albumin, erythropoietin, cellobiohydrolase, endocellulase, beta-gluosidase, xylanase and the like.

In addition, the present invention provides a method of producing a target protein in a plant characterized in that a plant is transformed with the above-described recombinant plant expression vector, and environmental stress, preferably drought stress, is applied to a resulting transgenic plant to produce a target protein in the plant. The target protein which can be obtained according to this method is the same as those described above.

Plant transformation means any method by which DNA is delivered to a plant. Such transformation method does not necessarily need a period for regeneration and/or tissue culture. Transformation of plant species is now quite general not only for dicot plants but also for monocot plants. In principle, any transformation method can be used for introducing a hybrid DNA of the present invention to appropriate progenitor cells. The method can be appropriately selected from a calcium/polyethylene glycol method for protoplasts (Krens, F. A. et al., 1982, Nature 296, 72-74; Negrutiu I. et al., June 1987, Plant Mol. Biol. 8, 363-373), an electroporation method for protoplasts (Shillito R. D. et al., 1985 Bio/Technol. 3, 1099-1102), a microscopic injection method for plant components (Crossway A. et al., 1986, Mol. Gen. Genet. 202, 179-185), a particle bombardment method for various plant components (DNA or RNA-coated) (Klein T. M. et al., 1987, Nature 327, 70), or a (non-complete) viral infection method in *Agrobacterium tumefaciens* mediated gene transfer by plant invasion or transformation of fully ripened pollen or microspore (EP 0 301 316), etc. A method preferred in the present invention includes *Agrobacterium* mediated DNA transfer. In particular, so-called binary vector technique as disclosed in EP A 120 516 and U.S. Pat. No. 4,940,838 can be preferably adopted for the present invention.

The "plant cell" that can be used for the plant transformation in the present invention can be any type of plant cell. It includes a cultured cell, a cultured tissue, a cultured organ or a whole plant. Preferably, it is a cultured cell, a cultured tissue, or a cultured organ. More preferably, it is a cultured cell in any form.

The term "plant tissue" can be either differentiated or undifferentiated plant tissue, including root, stem, leaf, pollen, seed, cancerous tissue and cells having various shape that are used for culture, i.e., single cell, protoplast, bud and callus tissue, but not limited thereto. Plant tissue can be in planta or in a state of organ culture, tissue culture or cell culture.

Further, the present invention provides a method for producing a transgenic plant comprising steps of:

transforming a plant cell with the recombinant plant expression vector of the present invention, and regenerating the above described transformed plant cell into a transgenic plant.

The method of the present invention comprises a step of transforming a plant cell with the recombinant vector of the present invention, and such transformation may be mediated by *Agrobacterium tumefaciens*. In addition, the method of the present invention comprises a step of regenerating a transformed plant cell to a transgenic plant. A method of regenerating a transformed plant cell to a transgenic plant can be any method that is well known in the pertinent art.

Further, the present invention provides a transgenic plant that is produced by the method described in the above. The plant according to the present invention can be food crops including rice, wheat, barley, corn, soy bean, potato, red bean, oat and millet; vegetable crops including *Arabidopsis thaliana*, Chinese cabbage, radish, hot pepper, strawberry, tomato, watermelon, cucumber, cabbage, melon, zucchini, scallion, onion and carrot; special crops including ginseng, tobacco, cotton, sesame, sugar cane, sugar beet, wild sesame, peanut and rapeseed; fruits including apple, pear, date, peach, kiwi, grape, tangerine, orange, persimmon, plum, apricot and banana; flowers including rose, gladiolus, gerbera, carnation, chrysanthemum, lily, and tulip; and feed crops including rye grass, red clover, orchard grass, alfalfa, tall fescue, and perennial rye grass. Preferably, the plant can be a monocot plant such as rice, barley, corn, wheat, rye, oat, sugar cane, onion and the like.

Further, the present invention provides a method of improving resistance of a plant to environmental stress by introducing the promoter of the present invention to a plant. The environmental stress can be preferably drought stress, but not limited thereto. This method can be carried out by operatively linking a structural gene which can improve resistance to stress to the promoter of the present invention and then introducing the resultant gene to a plant. The structural gene which can improve resistance to stress encodes a protein which is responsible for improving resistance of a plant to environmental stress such as dehydration, low temperature, or salt stress, etc. Examples of such protein are as follows: LEA protein; water channel protein; a synthetic enzyme for a common solute; tobacco detoxifying enzyme; an enzyme for synthesis of a substance which regulates osmotic pressure (e.g., sucrose, proline or glycine betaine); a gene which encodes omega-3 fatty acid desaturase of *Arabidopsis thaliana*, which is an enzyme for altering composition of a cell membrane and a gene which encodes D9-desaturase of cyanobacteria; P5CS, which is a main enzyme for proline synthesis, and; AtGolS3 gene for galactinol synthesis.

Still further, the present invention provides a primer set for amplification of the promoter of the present invention, consisting of a nucleotide sequence of SEQ ID NO: 2 and SEQ ID NO: 3.

The primer can be an oligonucleotide which consists of a fragment of at least 16, at least 17, at least 18, at least 19, at least 20, at least 21, at least 22, at least 23, at least 24, at least 25, at least 26, and more than 27 consecutive nucleotides of SEQ ID NO: 2.

The primer can be an oligonucleotide which consists of a fragment of at least 16, at least 17, at least 18, at least 19, at least 20, at least 21, at least 22, at least 23, at least 24, and more than 25 consecutive nucleotides of SEQ ID NO: 3.

In the present specification, the term "primer" indicates a single-stranded oligonucleotide sequence which is complementary to a nucleic acid strand to be copied, and it can be a starting point for synthesis of a primer extension product. Length and sequence of a primer are selected so as to allow the synthesis of a primer extension product. Specific length and sequence of a primer are determined in view of primer use condition such as temperature, ionic strength and the like, as well as complexity of a target DNA or RNA.

According to the present invention, an oligonucleotide which is used as a primer may also comprise a nucleotide analogue such as phosphorothioate, alkyl phosphorothioate or peptide nucleic acid, and also an intercalating agent.

The present invention will now be described in greater detail with reference to the following examples. However, it is only to specifically exemplify the present invention and in no case the scope of the present invention is limited by these examples.

EXAMPLES

Example 1

Isolation of Genomic DNA from Whole Rice Plant

Leaves of an about three-week old rice plant (Dong-jin variety, *Oryza sativa* L., 1 gram) were harvested and frozen in liquid nitrogen, and then by using a pulverizer leaf powder was prepared. With a DNeasy Plant mini kit (Qiagen), 100 g of the leaf powder was added with 400 ul AP1 and 4 ul RNaseA. The mixture was kept at 65° C. for 10 minutes. After adding 130 ul of AP2, the mixture was kept on ice for 5 minutes followed by centrifuge at 14000 rpm for 2 minutes. Then, to remove polysaccharides, the supernatant was introduced to a spin column in divided portions (650 ul each) and centrifuged. The aqueous solution was collected and added with AP3/E which is 1.5-fold the amount of the solution. The mixture was added to a DNA binding column in divided portions (650 ul each) and centrifuged at 8000 rpm for 1 minute. After washing twice with AW buffer (500 ul), the column was dried well and then dissolved in sterilized water (100 ul).

Example 2

PCR Cloning of 1859 bp 972 Gene Promoter

Figure 1:
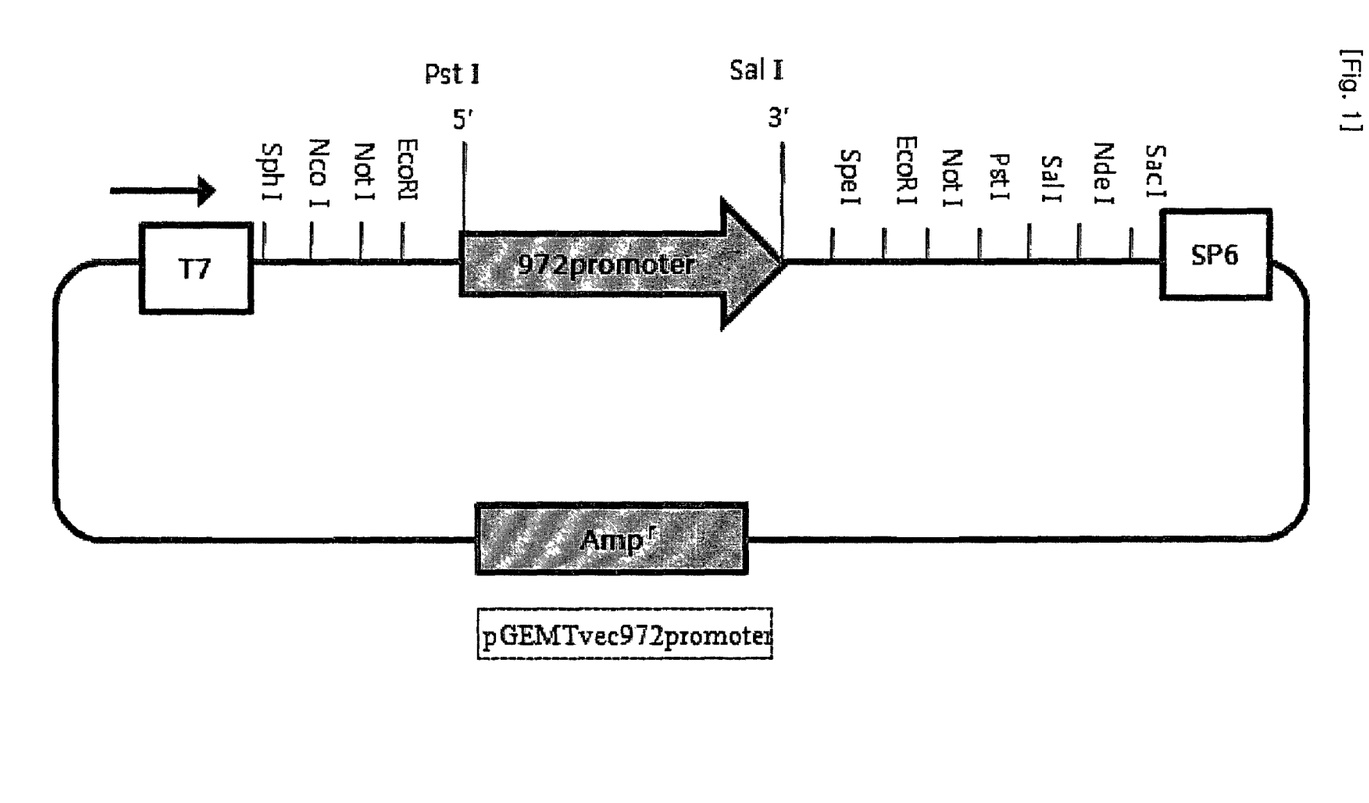
FIG. 1 is a schematic diagram showing pGEMTvec972 promoter for drought stress-inducible 972 promoter isolated from rice.

For cloning 972 promoter, a gene-specific primer set of 972pro5'-PstI: 5'-CTGCAGCACCTCTTTACAACTATG-GCCT-3' (SEQ ID NO: 2) and 972pro3'-SalI: 5'-GTCGACT-TGAGATGAGGCAGAGAGAT-3' (SEQ ID NO: 3) was used and the genomic DNA was amplified by polymerase chain reaction (PCR). PCR reaction solution comprised DNA 200 ng, 10X ExTaq polymerase buffer solution (pH 8.0), 200 mM dNTPs, 5X BandDoctor, 10 pmole of each primer and 5 U ExTaq polymerase (Takara Bio.). The reaction was started without adding any enzyme, and then amplification was carried out according to the following condition: 1 cycle including heating at 95° C. for 5 minutes as pre-denaturation step; 35 cycles including heating at 95° C. for 1 minute, 64° C. for 1 minute and 72° C. for 2 minutes, and; 1 cycle including heating at 72° C. for 10 minutes as a post-extension in Gene-Amp PCR system 9700 amplifier (Applied Biosystem). Major products that had been obtained from the amplification by PCR was gel-purified by using Gel Purification Kit (Bioneer, Korea). After subsequent cloning into pGEM-T easy vector (Promega, USA), the plasmid construct pGEMTvec972 promoter (FIG. 1) was produced according to the manufacturer's instruction, and then sequenced (SEQ ID NO: 1).

Example 3

Construction of a Vector for 972 Promoter Expression

Figure 2:
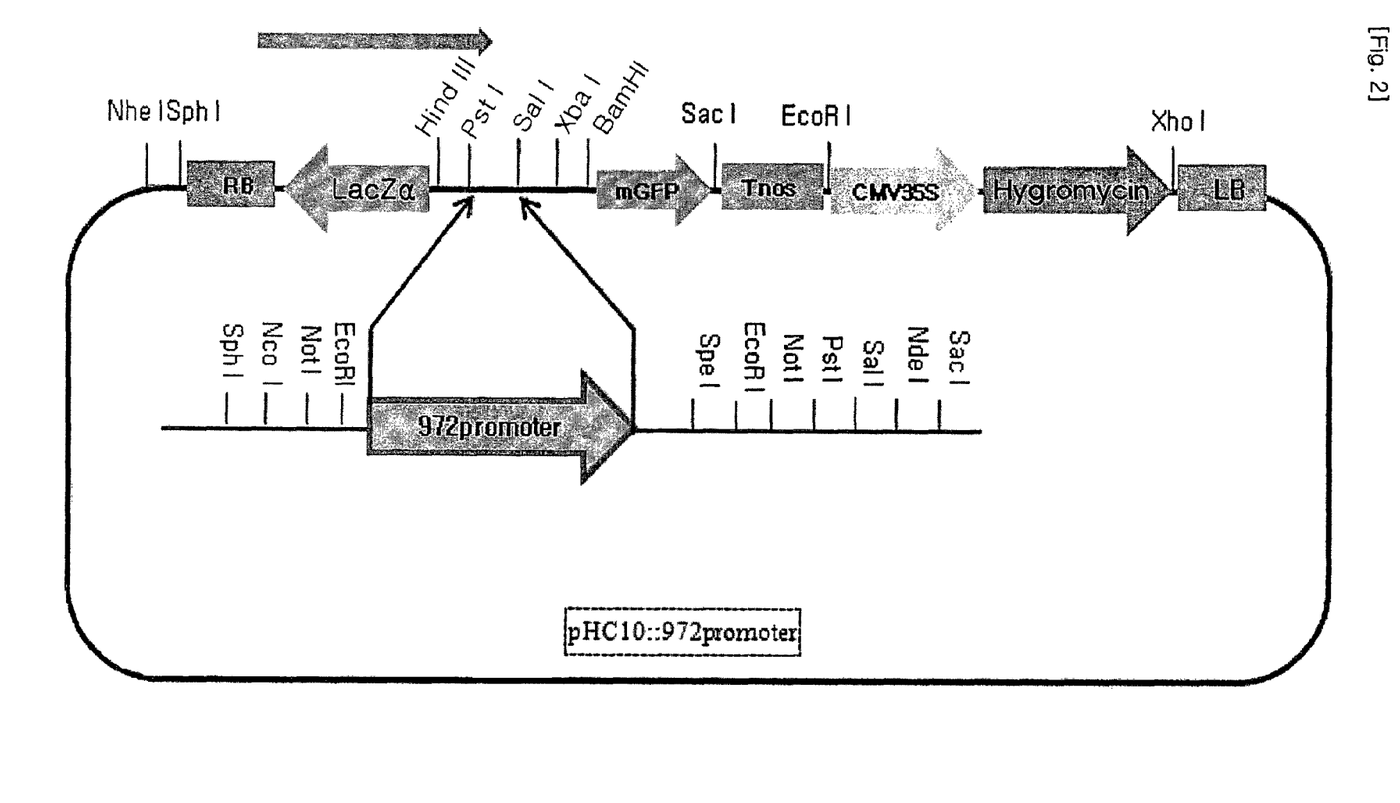
FIG. 2 is a schematic diagram showing pHC10:972 promoter vector for transformation delivery of drought stress-inducible 972 promoter isolated from rice.

DNA fusion construct for the promoter which comprises a reporter gene encoding mGFP was constructed as follows. For easy cloning into a binary vector pHC10, plasmid pGEMTvec972 promoter was digested with PstI and SanI, and then subcloned into PstI and SalI sites of pHC10. These clones were named pHC10:972 promoter, and an expression vector for delivery of plant transformation was produced (FIG. 2).

Example 4

Evaluation of the Function of 972 Promoter Gene Under Drought Stress-RT-PCR Analysis Three-week old rice leaves were dried (for 0 hr, 6 hr, 12 hr or 24 hr) and after pulverizing them with liquid nitrogen freezing, 100 mg of thus-obtained powder was added with TRI reagent (1 ml), and left at room temperature for 5 minutes. Bromochloropropane (0.1 ml) was added, followed by maintaining the mixture at room temperature for 15 minutes and centrifuge at 4° C., 12000 rpm for 15 minutes. Only the supernatant was transferred to a new tube, added with isopropanol (0.65-fold amount) and the mixture was kept at room temperature for 10 minutes. After centrifuge at 4° C., 12000 rpm for 15 minutes, RNA pellet was washed with 75% DEPC-ethanol, dried and dissolved in 30 ul solution. Gel-electrophoresis was carried out (1% agarose-formaldehyde gel) for identification, and by using 5 ug of the total RNA, $1^{st}$ cDNA was synthesized according to the following condition: total RNA 5 ug, Oligo dT (10 pmole), and 10 mM dNTPs were added and the mixture was heated at 65° C. for 5 minutes; 5X First strand buffer, 0.1 M DTT, and RNaseOut (40 U/ul) were added and the mixture was heated at 42° C. for 2 minutes and; SuperScript™ II (200 units) was added and the mixture was heated at 42° C. for 50 minutes and further at 72° C. for 15 minutes. The resultant was used for PCR determination. By using a primer set of 972 GSP-F: 5'-ACTCCTC-CTCCTGCTGCCAC-3' (SEQ ID NO: 4) and 972 GSP-R: 5'-GAAGCACATGTCGAGGAGGC-3' (SEQ ID NO: 5), PCR amplification was carried out according to the following condition: 1 cycle including heating at 95° C. for 5 minutes as pre-denaturation step; 25 cycles including heating at 95° C. for 30 seconds, 58° C. for 30 seconds and 72° C. for 30 seconds, and; 1 cycle including heating at 72° C. for 5 minutes as a post-extension in GeneAmp PCR system 9700 amplifier (Applied Biosystem). Major products that had been amplified by PCR were confirmed by gel-electrophoresis (2.5% agarose gel; see FIG. 3).

Figure 3:
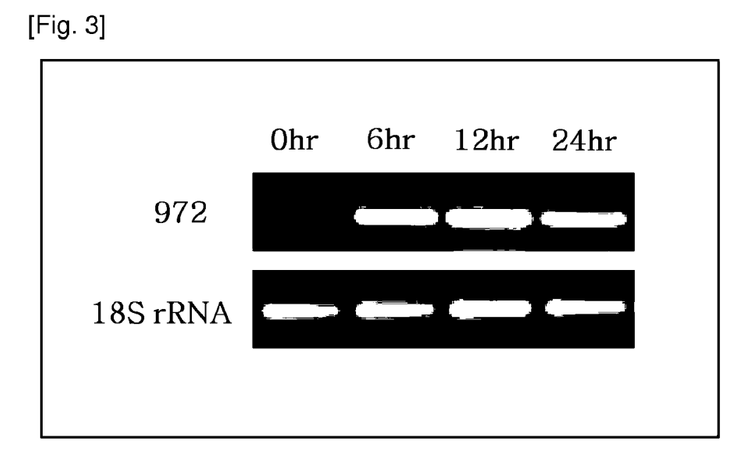
FIG. 3 is a RT-PCT result showing the expression of drought stress-inducible 972 promoter gene isolated from rice.

As it is shown in FIG. 3, compared to the rice leaves which did not receive any drought stress, gene expression was increased in the rice leaves which received drought stress. Thus, it was found that the promoter of the present invention is a drought stress-inducible promoter.

Example 5

GFP Determination After Transformation into Rice Callus pHC10:972 promoter vector was introduced to the rice plant (Dong-jin variety, *Oryza sativa* L.) based on *Agrobac-* terium-mediated vacuum infiltration method. To select a hygromycin resistant gene variant, unpolished rice in which testa was removed for callus formation was used as rice seeds. For the removal of testa, a simple rice polishing machine was used and the rice seeds with removed testa were sterilized once with 70% ethanol for 10 minutes, followed by 30 minutes sterilization in 2 to 3% sodium hypochlorite solution and washing with sterilized water at least three times. The rice seeds obtained after the sterilization were placed on a medium for callus formation (i.e., 10 to 12 seeds per medium) and incubated under dark condition at 28° C. for 3 to 4 weeks. Then, light yellow callus (1 to 2 mm diameter) was selected and cultured in 2N6 medium for three days. Meanwhile, the day after the callus selection, *Agrobacterium* was added to a medium comprising carbenicillin and hygromycin and cultured under dark condition at 28° C. for 3 to 5 days. After transferring the callus which had been cultured for three days, it was co-cultured in suspension comprising *Agrobacterium* and further cultured under dark condition at 25° C. for 3 days. The resulting co-cultured callus was washed with sterilized water comprising carbenicillin and the transformed callus was cultured under dark condition at 28° C. for 2 to 3 weeks. Healthy callus showing good growth was selected again. After the transfer to a new medium, the callus was again cultured under the same condition. Healthy callus was then again added to a regeneration selection medium. The transformant in which the target gene had been introduced was identified by genomic PCR.

GFP Determination

In order to examine the function of 972 promoter, an ELISA analysis using an GFP antibody was carried out. Specifically, after applying 0 hr or 6 hr drought stress to the transformant leaf which had been selected by genomic PCR, total protein was extracted by using a solution comprising 50 mM Tris-HCl (pH 7.5), 1 mM EDTA, 8 mM $MgCl_2$, and a proteinase inhibitor. Thus-obtained total protein was quantified by using Bradford assay solution, and 10 ug of the protein was used for the determination. In a microplate, the antigen comprising 200 ul coating buffer and the total protein was added and reacted at 4° C. for 12 hours. After blocking with 1×PBS comprising 4% skim milk for two hours at room temperature, GFP antibody was diluted to 1/4000 with 1×PBS comprising 1% skim milk and was allowed to bind to the antigen by incubating them at room temperature for 2 hours. 1×PBS comprising 0.05% Tween 20 was used for washing, and the secondary antibody was diluted to 1/2000 with 1×PBS comprising 1% skim milk and was allowed to bind to the antigen by incubating them at room temperature for 1 hour followed by washing. After the development with a solution comprising 30% $H_2O_2$, PC buffer and OPD, the reaction was terminated by adding 2.5M $H_2SO_4$. Then, the absorbance at 490 nm was determined by using a microplate reader and the result was analyzed (FIG. 4).

Figure 4:
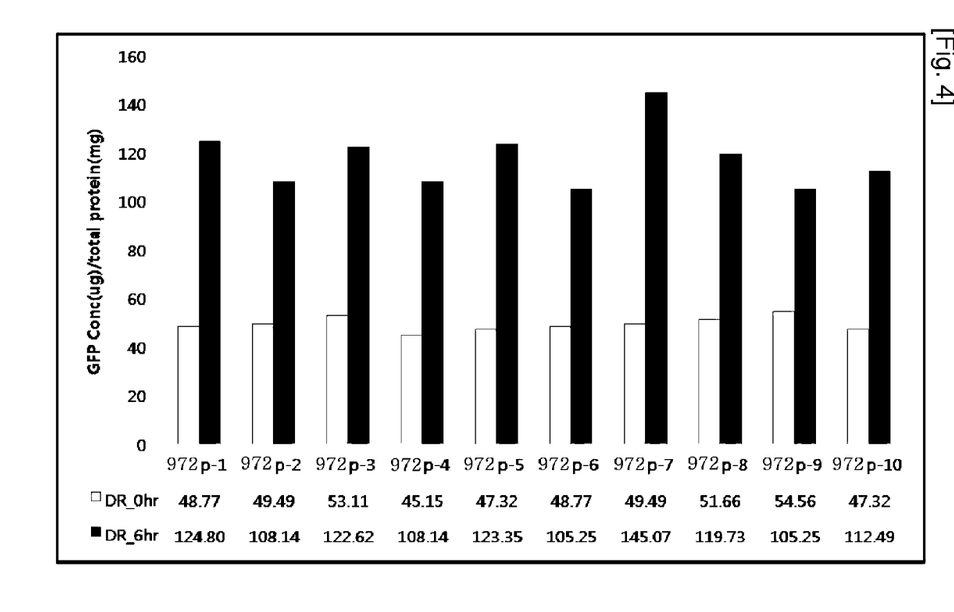
FIG. 4 is a GFP assay result for determination of the expression of drought stress-inducible 972 promoter gene isolated from rice. 972p-1, -2, -3, -4, -5, -6, -7, -8, -9 and -10 each represent an independently-transformed plant.

As it is shown in FIG. 4, compared to the transgenic rice which did not receive any drought stress, GFP expression was significantly increased in the transgenic rice which received drought stress. Thus, it was found that the promoter of the present invention is a drought stress-inducible promoter.

The invention claimed is:

1. Environmental stress-inducible 972 promoter isolated from rice which consists of nucleotide sequence of SEQ ID NO: 1.

2. The promoter according to claim 1, characterized in that the environmental stress is drought stress.

3. A recombinant plant expression vector comprising the promoter of claim 1.

4. The recombinant plant expression vector according to claim 3, which is constructed by operatively linking a target gene encoding a target protein to a downstream region of the promoter.

5. A method of producing a target protein in a plant, characterized in that a plant is transformed with the recombinant plant expression vector of claim 4 and drought stress is applied to a resulting transgenic plant to produce the target protein in the plant.

6. The method according to claim 5, characterized in that the target protein is selected from a group consisting of interleukin, interferon, platelet-derived growth factor, hemoglobin, elastin, collagen, insulin, fibroblast growth factor, human growth factor, human serum albumin, erythropoietin, cellobiohydrolase, endocellulase, beta-gluosidase, and xylanase.

7. A method for producing a transgenic plant comprising steps of:
    transforming a plant cell with the recombinant plant expression vector of claim 3, and
    regenerating the above described transformed plant cell into a transgenic plant.

8. A transgenic plant which is produced according to the method of claim 7.

9. The transgenic plant according to claim 8, characterized in that said plant is a monocot plant.

10. A method of improving resistance of a plant to environmental stress by introducing the promoter of claim 1 to a plant.

11. The method according to claim 10, characterized in that the environmental stress is drought stress.

12. A primer set for amplification of the promoter of claim 1, consisting of nucleotide sequence of SEQ ID NO: 2 and SEQ ID NO: 3.

* * * * *